United States Patent
Glenn et al.

(10) Patent No.: US 6,607,390 B2
(45) Date of Patent: Aug. 19, 2003

(54) SYSTEM AND METHOD FOR LONGITUDINAL ANALYSIS OF MOOD DISORDERS

(76) Inventors: Tasha Glenn, 1037 E. Brookdale Pl., Fullerton, CA (US) 92831; Peter C. Whybrow, Box 37, 100 Daniels Rd., Plainfield, NH (US) 03781

(\*) Notice: Subject to any disclaimer, the term of this patent is extended or adjusted under 35 U.S.C. 154(b) by 0 days.

(21) Appl. No.: 09/915,790

(22) Filed: Jul. 26, 2001

(65) Prior Publication Data

US 2002/0150872 A1 Oct. 17, 2002

Related U.S. Application Data

(60) Provisional application No. 60/266,588, filed on Feb. 6, 2001.

(51) Int. Cl.[7] ............................................... G09B 19/00
(52) U.S. Cl. ..................................................... 434/236
(58) Field of Search ................... 434/238, 237, 434/236, 430

(56) References Cited

U.S. PATENT DOCUMENTS

| 5,511,981 A | * | 4/1996 | Olsen | 434/238 |
| 6,063,028 A | * | 5/2000 | Luciano | 128/898 |
| 6,075,755 A | * | 6/2000 | Zarchan | 221/3 |
| 6,311,644 B1 | * | 11/2001 | Pugh | 119/712 |
| 6,334,778 B1 | * | 1/2002 | Brown | 273/429 |

\* cited by examiner

Primary Examiner—Henry C. Yuen
Assistant Examiner—Hyder Ali

(57) ABSTRACT

In a computer system having a storage device, a method for gathering clinical data useful in the clinical analysis and treatment of mood disorders. The method includes such steps as displaying a main menu including a multiplicity of icons depicting inquiries to be answered by a patient; and, storing the patient's answers to the inquiries as clinical data generated on a regular basis by the patient. The method further includes selecting a point on a scale depicting the patient's current mood; selecting a sleep icon for updating sleep data; and, selecting a medication icon for updating type and amount of medication taken. The present invention is also capable of creating longitudinal charts and statistics based on selections made by a patient over a given period of time.

24 Claims, 15 Drawing Sheets

FIG. 10

SYSTEM AND METHOD FOR LONGITUDINAL ANALYSIS OF MOOD DISORDERS

CROSS REFERENCE TO RELATED APPLICATION

This Application claims the benefit of U.S. Provisional Patent Application, Serial No. 60/266,588, entitled System for Longitudinal Analysis of Bipolar Disorder, filed Feb. 6, 2001.

1. FIELD OF THE INVENTION

This invention relates in general to mental health, and in particular to a system and method useful in the treatment of mood disorders.

2. BACKGROUND OF THE INVENTION

A bibliography for the following text appears at the end of the specification and before the claims hereof. Mood disorders are mental illnesses in which a person experiences emotions outside the normal boundaries of sadness and elation. The most commonly occurring mood disorder is a major depressive disorder, which features one or more episodes of depression (APA 1994). Bipolar disorder features one or more episodes of mania or episodes of both mania and depression (APA 1994). Other mood disorders are dysthymia (persistent low-grade depression) and cyclothymia (mild moodswings).

Mood disorders occur commonly. In the USA, the National Comorbidity Study showed a lifetime prevalence of 17% for major depressive disorder and 1.6% for bipolar disorder (Kessler 1994).

Mood disorders are associated with high morbidity and mortality. Despite current treatments, episodes recur frequently. Following an initial episode, the probability of recurrence in major depressive disorder is 50–85% (Mueller 1999). In bipolar disorder, the probability of recurrence by 5 years is 90% (Tohen 1990). Dysthymia is associated with a marked increase in risk of developing major depressive episodes. (Keller Shapiro 1982).

Many patients do not obtain full recovery between episodes. In 20–30% of those with major depressive disorder, the depressive symptoms persist for longer than a year after treatment of the acute phase and 12% do not recover by 5 years (Keller 1992). In bipolar disorder, episodes of mania and depression are often protracted with 24% of patients remaining acutely ill after 1 year, 16% after 2 years and 9% after 5 years (Keller 1993). Many patients with depressive disorder or bipolar disorder report residual symptoms that impose considerable morbidity despite successful treatment (Fava 1999). As a consequence, many patients with bipolar disorder (Gitlin 1995) and major depressive disorder (Thase 1995) will develop a chronic and disabling course. Both major depressive disorder and bipolar disorder are among the top ten causes of worldwide disability (Murray 1996).

Mood disorders have a large economic impact on society. The costs of depression are estimated to be similar to those of cancer and ischemic heart disease, due to reduced productivity and increased use of healthcare resources (Greenberg 1993). A 1991 report from the National Institutes of Mental Health estimated the annual costs of bipolar disorder to be $45 billion (Wyatt 1991).

The disability and suffering in mood disorders impacts all aspects of life. Psychosocial impairment has been found to persist for years after an episode of mania or depression even for patients in remission (Coryell 1993). Mood disturbances are associated with high workplace absenteeism (Broadhead 1990) and poor well-being compared to those with chronic medical illnesses (Wells 1990).

Suicide is the most severe complication of mood disorders. Patients with major depressive disorder or bipolar disorder are more likely to attempt or complete suicide than any other medical group (Goodwin and Jamison 1990). A review of 31 studies of patients with major depressive disorder or bipolar disorder found a lifetime prevalence of suicide ranging from 9 to 60% (Goodwin and Jamison 1990).

The treatment of mood disorders is complex and usually requires a patient to take multiple medications several times a day. Maintenance therapy to prevent a recurrence of major depressive disorder may last several years or more. Maintenance therapy for bipolar disorder is usually for the patient's lifetime.

Most medications used to treat psychiatric disorders have uncomfortable side effects such as weight gain, tremors, hair loss and cognitive dulling. Although the combinations of drugs needed to treat mood disorders improve response, they also increase side effects and patient costs. Polypharmacy schedules can be difficult to adhere to. Thus, an understanding of the disorder and long-term commitment to the treatment is needed from the patient. Patient non-compliance with medication is a serious problem and the major factor that accounts for patient relapse. Studies show rates of non-compliance with maintenance therapy in between 24–53% of patients with major depressive or bipolar disorders (Schumann 1999, Simon 1993, Aagaard 1988, Berghofer 1996).

Daily patient self-reporting of mood and sleep is well established as a valuable clinical tool (Bauer 1991; Leverich and Post 1996). Mood disorders are characterized by rapid changes in mood making treatment decisions difficult. The prospective semi-continuous measure of infradian (daily or longer) fluctuations of patients' mood and sleep allows for detailed assessment of frequency and pattern of illness (Denicoff 1997). Simultaneous comparison of daily mood fluctuations and medications may help to optimize and rationalize complex pharmacological therapy and to better detect nuances of partial response (Post 1997). Another benefit of daily self-reporting of mood is increased patient involvement in their care.

Two methodologies are currently used for daily patient self-reporting of mood: the Life Chart Methodology (Leverich and Post 1996) and the Chronosheet developed by Whybrow in the 1970s. The latter uses a 100-mm visual analogue scale (VAS) between the mood extremes of mania and depression on which the patient marks mood proportionately (Bauer M S 1991). The Chronosheet also records sleep, weight, psychiatric medications and life events. Both self-rating methodologies are paper and pencil based. The patient is given a form or booklet to complete by hand daily. The patient returns the completed form to staff monthly for data entry into a computer for analysis. There are several problems with a paper-based process. Data entry is very time-consuming and expensive. Overall data quality is negatively impacted by data entry errors. It is then necessary to manually digitize the VAS data for computer entry. Any data transformations performed by humans provide additional opportunities for error.

Accordingly, there is a need for a method and system to automate patient charting that is simple for patients to use and will provide physicians with an immediate display and data analysis of the results. More specifically, there is a need for an automated system that will record longitudinal data useful in the treatment of mood disorders, such as mood, sleep, medications, life events, weight changes and menstrual data. Moreover, there is a need for a system that will automatically provide a time-based visual display of the relationships between changes in mood, sleep, medications, life events, weight and menstrual data.

SUMMARY OF THE INVENTION

The present invention is a system and method for providing immediate longitudinal analysis of patient data to assist clinicians with treatment of mood disorders. Patients are enrolled in an administrative system on a computer at the physician's office. Patients are trained to install software on a home computer and then taught how to enter data accurately. A graphical user interface makes the software easy and fast for daily patient use. Patients enter their mood, sleep, medications taken, life events; and, if female menstrual data, every day and weight weekly. Patients without a home computer can use a computer at a mental health facility. Patients return data to the administrative system via E-Mail over the Internet or via diskette. Clinicians can obtain both descriptive charts and statistical analyses of all collected patient data in the administrative system.

This invention overcomes current deficiencies and allows a patient to enter daily mood and other clinical data directly into a home computer or into a computer at a mental health facility.

An advantage of the present invention is that clinicians can immediately obtain both descriptive charts and statistical analyses of the collected patient data to assist with clinical decision-making.

Another advantage of the present invention is that an automated charting system may be perceived by the patient more positively wherein one may be more apt to cooperate rather than with using a paper and pencil system, thereby improving compliance.

Another feature of the present invention is that data may be collected, displayed and analyzed in perpetuity for individual patients. Any time period in a patient's data can be selected for immediate display and analysis.

Another feature of the present invention is that data from multiple patients may be easily aggregated for use in clinical research.

These and other objects, which will become apparent as the invention is described in detail below, are provided in a computer system having a storage device, a method for gathering clinical data useful in the clinical analysis and treatment of mood disorders. The method includes such steps as displaying a main menu including a multiplicity of icons depicting inquiries to be answered by a patient; and, storing the patient's answers to the inquiries as clinical data generated on a regular basis by the patient. The method further includes selecting a point on a scale depicting the patient's current mood; selecting a sleep icon for updating sleep data; and, selecting a medication icon for updating type and amount of medication taken. The present invention is also capable of creating longitudinal charts and statistics based on selections made by a patient over a given period of time.

Still other objects, features and advantages of the present invention will become readily apparent to those skilled in the art from the following detailed description, wherein is shown and described only the preferred embodiment of the invention, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive, and what is intended to be protected by Letters Patent is set forth in the appended claims. The present invention will become apparent when taken in conjunction with the following description and attached drawings, wherein like characters indicate like parts, and which drawings form a part of this application.

BRIEF DESCRIPTION OF THE DRAWINGS

The general purpose of this invention, as well as a preferred mode of use, its objects and advantages will best be understood by reference to the following detailed description of an illustrative embodiment with reference to the accompanying drawings in which like reference numerals designate like parts throughout the figures thereof, and wherein:

FIG. 10 illustrates the mood dialog box of the patient data entry program of the present invention.

DETAILED DESCRIPTION OF THE INVENTION

Figure 1:
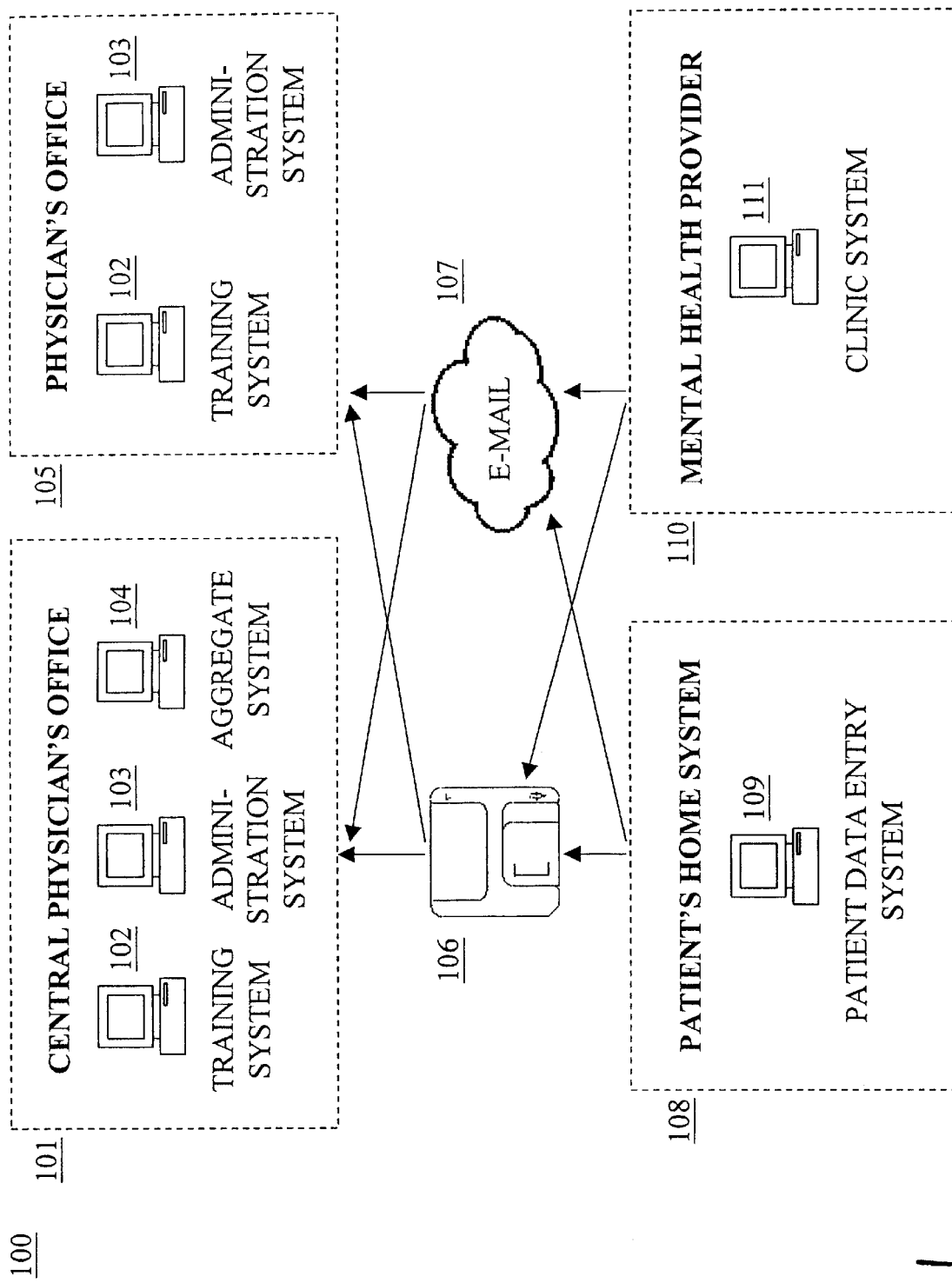
FIG. 1 is a pictorial representation of a data processing system used to implement a method and system of the present invention.

FIG. 1 depicts the components of an example system 100 for longitudinal analysis of mood disorders. At a central physician's office 101 the system 100 for longitudinal analysis of mood disorders contains computers used for training patients 102, system administration 103 and for aggregating data from multiple patients and from multiple sites 104. Another physician office 105 may have a computer with a training system 102 and a computer 103 for system administration. The system administration computer 103 is used to enroll patients, receive and analyze data and display or print reports. The training computer 102 is used to train patients on how to install and use the software at home or at a clinic. Mental health providers, such as a day treatment facility 110, contain clinic system computers 111 for data entry by patients who do not have a computer at home. Patients with a computer at home 108 install a patient data entry system software 109. Every day patients enter mood data directly onto the software on their home computer 109. Patients return data to the system administration computer 103 at the physician's office 101 or 105, by E-Mail over the Internet 107 or via diskette 106. Patient data from clinic systems computers 111 likewise is returned to the system administration computer 103 by E-Mail over the Internet 107 or via diskette 106. After patient data is returned, mood charts and statistical charts are displayed or printed on the system administration computer 103 in the physician's office 101 or 105.

If the patient data collection is part of a research study, data from all physician office sites 105 is returned to the aggregate system 104 in the central physician's office 101 by E-mail over the Internet 107 or via diskette 106. The aggregate system 104 will merge the data of all patients from all sites, remove all patient identifiers and format the output file for analysis in commercial programs.

Figure 2:
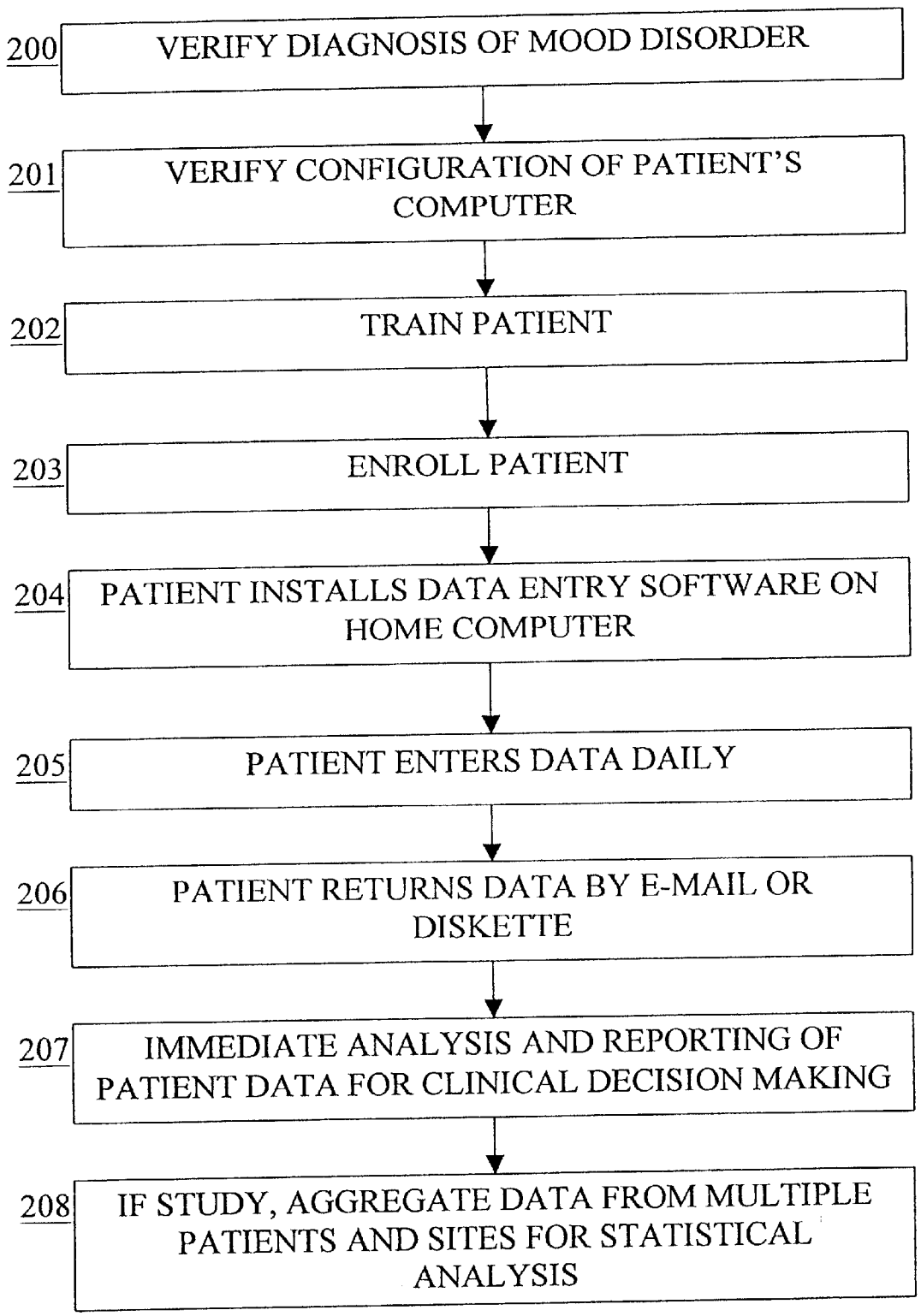
FIG. 2 is a block diagram of the overall method for providing longitudinal analysis of mood disorders.

FIG. 2 illustrates a method to provide longitudinal analysis of mood disorders in accordance with the present invention. The system 100 of FIG. 1 can be used to implement the method of FIG. 2. The first step is to verify the patient's diagnosis (step 200) to ensure that the patient has a mood disorder. After determining the patient is an appropriate candidate for mood charting, the configuration of the computer the patient has at home is verified (step 201). If the configuration of the home computer is adequate, the patient is trained to use the software (step 202) at the physician's office. The training includes a demonstration of how to install the software on a home computer, instructions on how to enter data accurately and an overview of mood charting. Next, the patient is enrolled (step 203) on the system administrator computer (103 of FIG. 1). The patient is then given software to install on their home computer (step 204). The patient installs the software on a home computer and enters data every day (step 205). Every month, or at a frequency determined by their physician, the patient returns data to the system administrator computer (103 of FIG. 1), either by E-Mail over the Internet or by diskette (step 206). The data from the patient is analyzed and reports are displayed and printed (step 207). If the patient is part of a research study, data from the physician site can be aggregated with data from other patients and study sites for statistical analysis (step 208).

Figure 3:
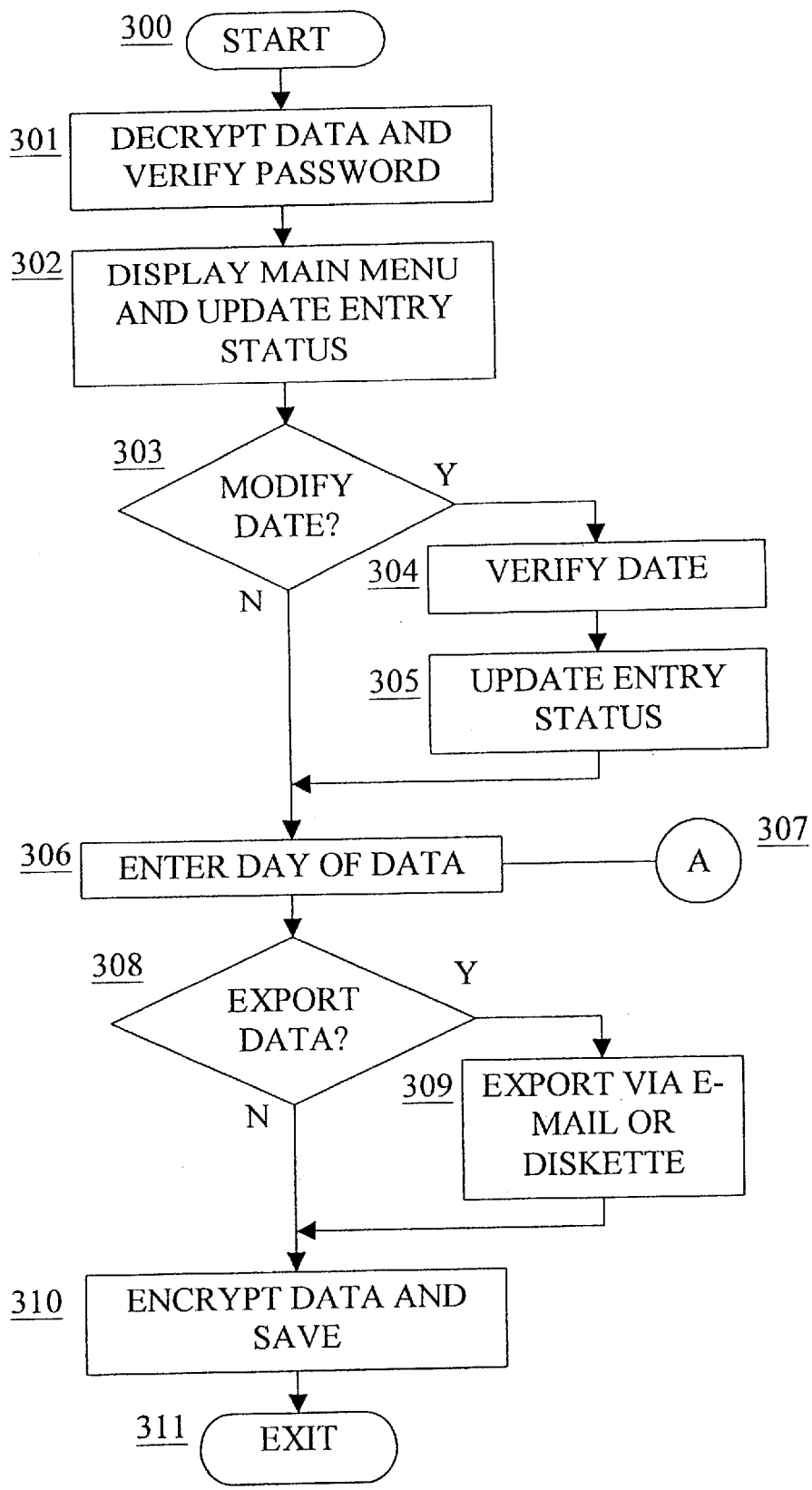
FIG. 3 is a high-level flow chart illustrating the operation of the program a patient installs on their home computer to enter data daily.
Figure 4:
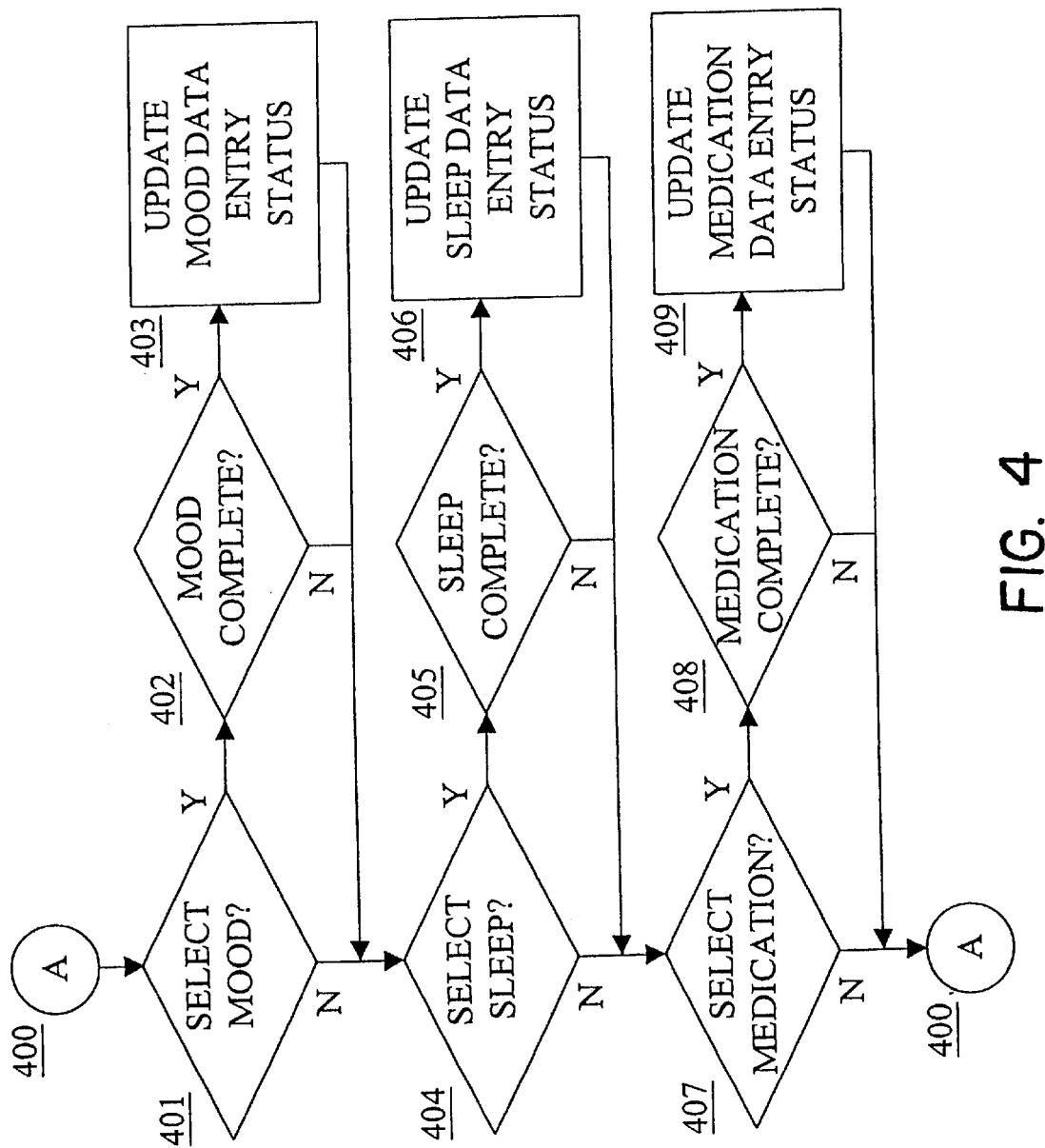
FIG. 4 is a more detailed flow chart of a portion of the method of FIG. 3.

FIGS. 3 and 4 are high-level flowcharts that refer to the operation of the software of the present invention, which is installed on a patient's computer at home. The process begins with a start bubble 300. The patient starts up the software and enters their password. The process then decrypts the patient's data file and verifies that the password is correct (block 301). After this, the main menu is displayed (block 302) and updates are made to the entry status for the current date. The entry status graphically displays whether the patient completed entry of all required data in each major section (mood, sleep, and medications).

An inquiry is then made to determine if the date is being changed (diamond 303). If the response is no, the process proceeds to the next step depicted by a block 306. If the response to decision block 303 is yes, block 304 verifies the new date selected. Any data previously entered for the selected date is retrieved and the entry status reset accordingly at block 305.

Block 306 allows entry of a day of data as in FIG. 4. Decision block 308 checks if the data is to be exported back to the clinic for analysis. If the response to decision block 308 is yes, block 309 encrypts all the patient's data for export by E-mail via Internet or by diskette. If the response to decision block 308 is no, the process proceeds to block 310 where the patient exits the program and data is encrypted and saved.

At connector A of FIG. 4, the process allows the entry of a day of data. Decision block 401 selects the main menu choice to allow entry of mood data. If the response to decision block 401 is no, the process proceeds to a decision block 404. On the other hand, if the response to decision block 401 is yes, the mood dialog box will appear and decision block 402 verifies that all required data has been entered.

Mood data is entered using a VAS scale between 0 and 100. The most extreme feelings of depression and mania the patient has ever experienced define the anchor points. The patient slides the scale to the number that best represents mood over the past 24 hours, in relation to these anchor points. Other data entered here are optionally any significant life events and, if female, menstrual data. If the response to decision block 402 is no, the process returns to decision block 401 to allow re-entry of the data. If the response to decision block 402 is yes, the data entry status for the mood section for the current date is updated to complete at block 403. The process proceeds to decision block 404.

Decision block 404 selects the main menu choice to allow entry of sleep data. If the response to decision block 404 is no, the process proceeds to decision block 407. On the other hand, if the response to decision block 404 is yes, the sleep dialog box will appear and decision block 405 will verify that all required data has been entered. For each hour of the day, a graphical toggle switch is used to select if awake, asleep or in bed and awake. If the response to decision block 405 is no, the present process returns to decision block 404 to allow re-entry of the data. On the other hand, if the response to decision block 405 is yes, the data entry status for the sleep section for the current date is updated to complete at block 406. Then the process proceeds to decision block 407.

Decision block 407 selects the main menu choice to allow entry of medication data. If the response to decision block 407 is no, the process proceeds to decision block 400 (FIG. 3) as denoted by the connector A. On the other hand, if the response to decision block 407 is yes, the medications dialog box will appear and decision block 408 will verify that all required data has been entered. Medications are displayed by trade and generic name, as well as strength. For each medication displayed, data is entered by the count of pills taken for the day. The strength of each pill and the number of pills can be changed. Current medications can be deleted and new medications can be selected from an internal list of psychotropic medications. If the response to decision block 408 is no, the process returns to decision block 400 (FIG. 3) to allow re-entry of the data. On the other hand, if the response to decision block 408 is yes, the data entry status for the medications section for the current date is updated to complete at block 409. Then the process proceeds to block 307 (i.e., connector A) of FIG. 3.

Figure 5:
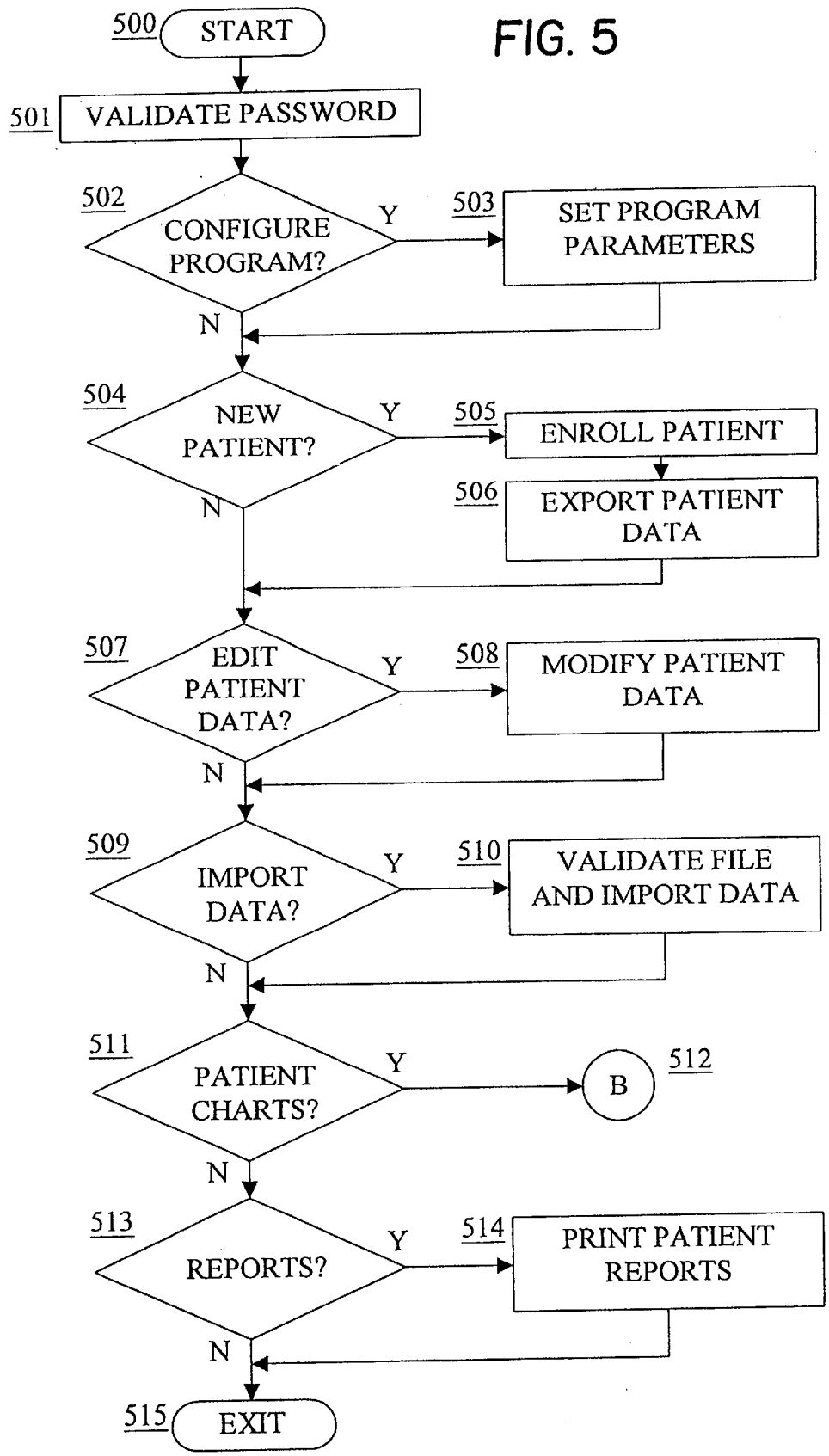
FIG. 5 is a high-level flow chart illustrating the operation of the administrative system program that is installed on a workstation in the physician's office.
Figure 6:
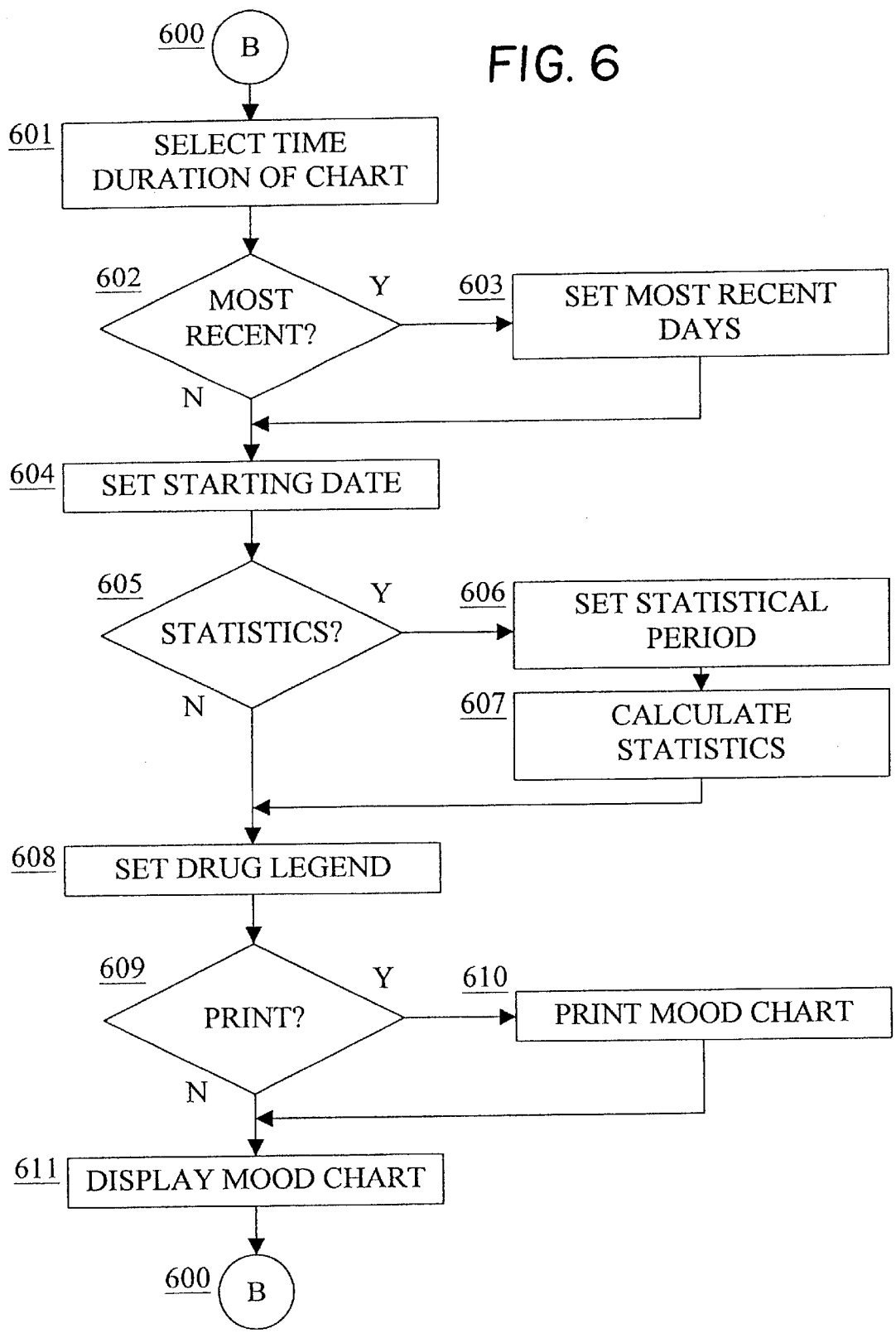
FIG. 6 is a more detailed flow chart of a portion of the method of FIG. 5.

FIGS. 5 and 6 are high-level flow charts that refer to the operation of the administrative system of the present invention, which is installed on a computer in the physician's office. In FIG. 5, block 501 validates the user's password. Decision block 502 allows changes to the system configuration. If the response to decision block 502 is no, the process proceeds to decision block 504. On the other hand, if the response to decision block 502 is yes, block 503 sets system parameters including system demographics, physician names, printing in color and use of pounds or kilograms.

Decision block 504 asks if there is a new patient to enroll in the system. If the response to decision block 504 is no, the process proceeds to decision block 507. On the other hand, if the response to decision block 504 is yes, a new patent is enrolled in block 505. Enrollment includes entering patient demographic information and defining patient specific anchor points on the mood scale. The patient selects a password that is easy to remember. Block 506 exports a patient specific file required for installation of the software on the patient's home computer or on a clinic system.

Decision block 507 allows patient demographic data to be modified. This does not refer to the daily mood data entered by the patient at home. This refers to patient demographic, diagnostic data (DSM-IV diagnoses with specifiers) entered during enrollment and test results (HAMD, YMRS, BDI, etc). If the response to decision block 507 is no, the process proceeds to decision block 509. On the other hand, if the response to decision block 507 is yes, block 508 modifies, adds and deletes patient data.

Decision block 509 checks if there is patient data ready for importing. If the response to decision block 509 is no the process proceeds to decision block 511. On the other hand, if the response to decision block 509 is yes, block 510 validates the import file and adds the data to the patient's folder.

Decision block 511 allows display and printing of mood charts as in FIG. 6 and denoted by a connector B. Block 601 sets the desired time duration of the mood chart. The duration may be 30, 60, 90 or 120 days. Decision block 602 allows the most recent days that meet the specified duration to be used. If the response to decision block 602 is no, the process proceeds to block 604. On the other hand, if the response to decision block 602 is yes, the most recent days that meet the specified duration are set.

Block 604 sets the starting date for the mood chart. Decision block 605 selects statistical charts. If the response to decision block 605 is no, the process proceeds to block 608. On the other hand, if the response to decision block 605 is yes, block 606 sets the period used for the statistical calculations to either 7 or 30 days. Block 607 makes the statistical calculations.

Block 608 sets the drug legend that annotates which medications the patient was taking. Decision block 609 determines if the mood chart should be printed. If the response to decision block 609 is no, the process proceeds to block 611. On the other hand, if the response to decision block 609 is yes, mood charts are printed at block 610. Block 611 displays the mood charts on the screen. Block 600 returns to FIG. 5 at the connector B.

Decision block 513 determines whether or not printing of patient reports on demographic, diagnostic and test result data is to be made. If the response to decision block 513 is no, the process proceeds to block 515. On the other hand, if the response to decision block 513 is yes, reports can be selected and printed (block 514). Thereafter the process exits (block 515).

Figure 7:
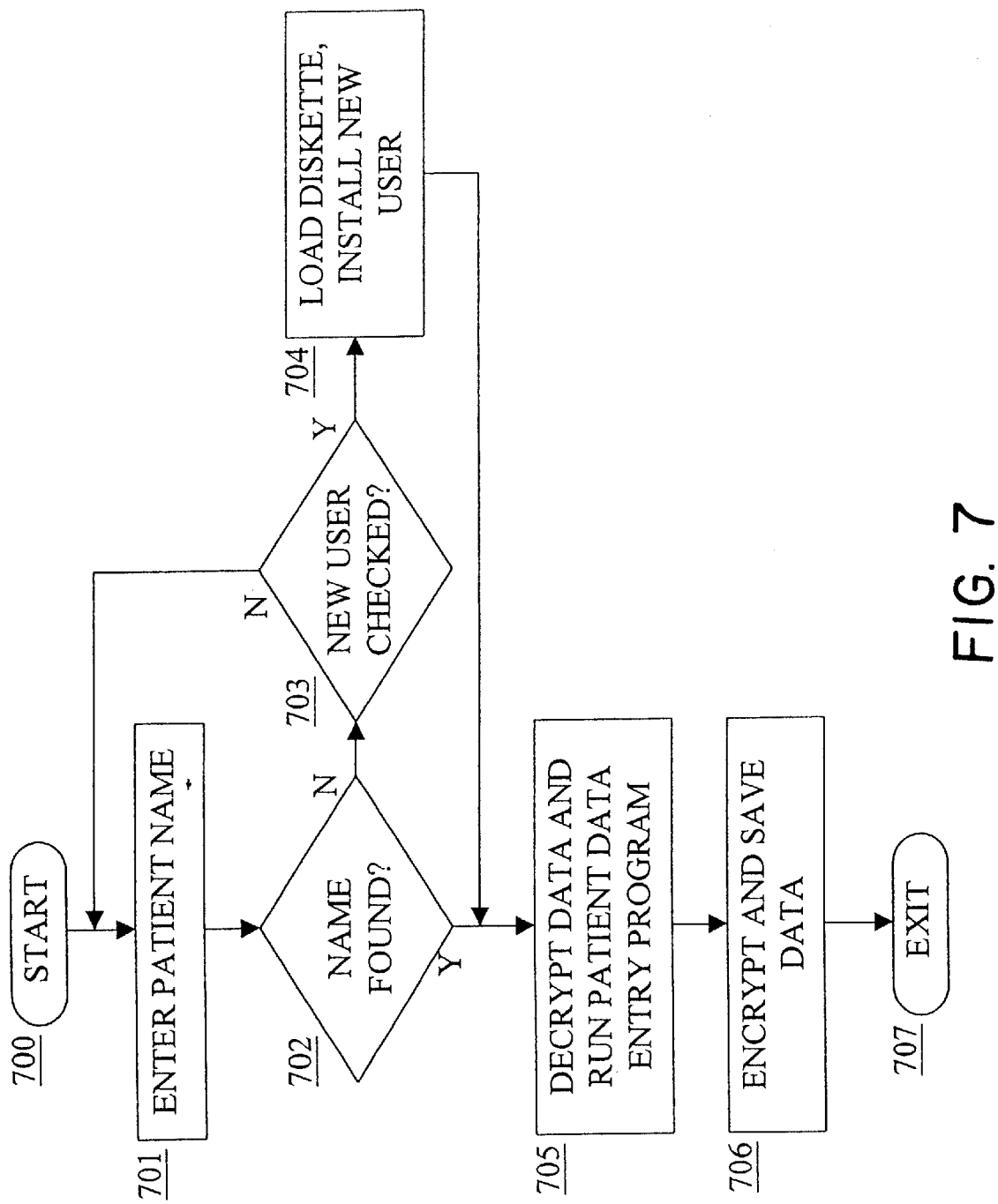
FIG. 7 is a high-level flow chart illustrating the operation of the program patients use to enter data in a workstation in a mental health clinic.

FIG. 7 is a high-level flow chart illustrating the operation of the program patients use to enter data on a computer in a mental health clinic. At block 701, the patient enters their name. Decision block 702 verifies the name is in the system. If the response to decision block 702 is yes, the process proceeds to block 705. On the other hand, if the response to block 702 is no, decision block 703 checks if this is a new user. If the response to decision block 703 is no, the system returns to block 701 for re-entry of the name. On the other hand, if the response to decision block 703 is yes, block 704 loads the program diskette and the patient is installed as a new user. After installation, the system returns to block 705.

Block 705 allows entry of patient data in a fashion identical to that described in FIG. 3 and FIG. 4. After data entry is finished in block 706 wherein the patient data is encrypted and saved; thereafter the process exits (bubble 707).

Figure 8:
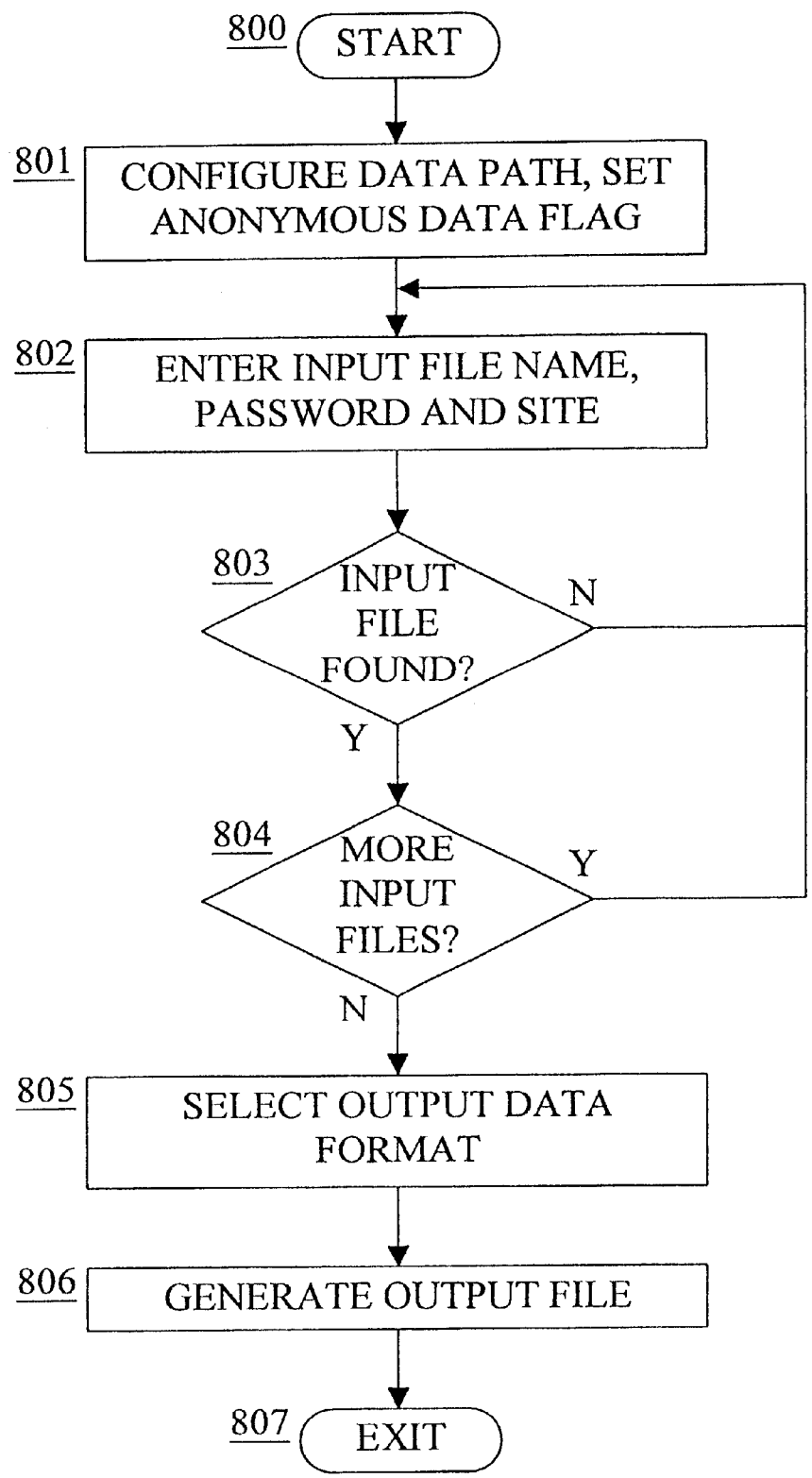
FIG. 8 is a high-level flow chart illustrating the operation of the program used to aggregate patient data from multiple sources for research.

FIG. 8 is a high-level flow chart illustrating the operation of the process used to aggregate patient data from multiple sources for research. The step depicted by a block 801 configures the aggregate system including setting the data path, and making all data anonymous (removing all fields that contain patient identifying information). At the step depicted by the block 802, the name of the file to be included is input, along with the input password and input site name. Decision block 803 finds the file described in block 802. If the response to decision block 803 is no, the system returns to block 802. If the response to decision block 803 is yes, the process proceeds to decision block 804 to check if there are more input files to merge. If the response to decision block 804 is yes, then the process returns to block 802. On the other hand, if the response to decision block 804 is no, block 805 selects a database, spreadsheet or text file output format for the aggregated data. The format selected will allow the aggregated data to load directly into popular spreadsheets, databases or statistical programs for analysis. Block 806 generates the output file of the aggregated data; thereafter the process exits (bubble 807).

Figure 9:
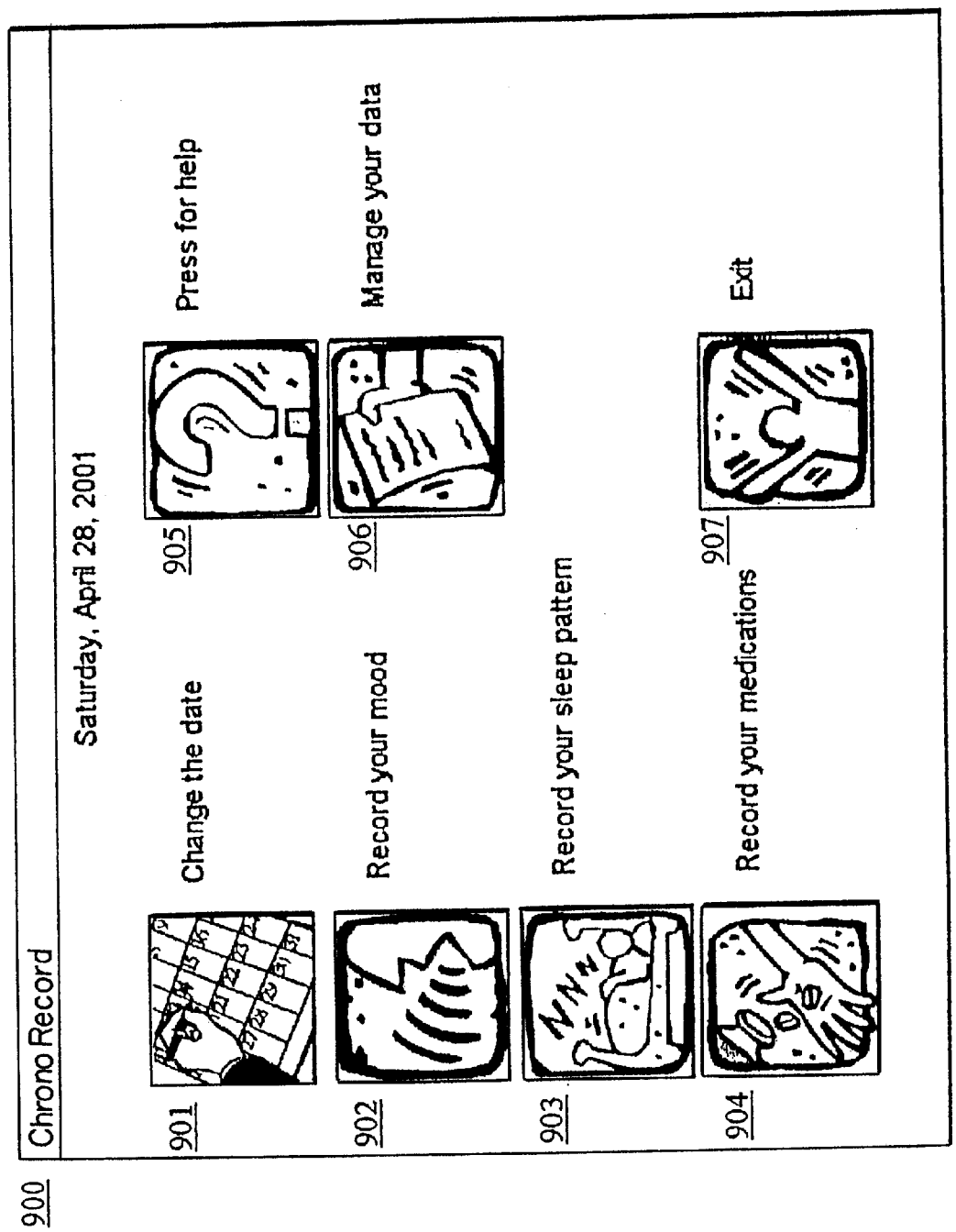
FIG. 9 illustrates the main menu of the patient data entry program of the present invention.

FIGS. 9 through 12 illustrate the screens used by the patient to enter data daily on a home computer. FIG. 9, view 900 shows the main menu screen with a graphical button to select all activities: change the date icon 901, record mood icon 902, record sleep pattern icon 903, record medications icon 904, online help icon 905, manage data icon 906 and exit icon 907.

Figure 10:
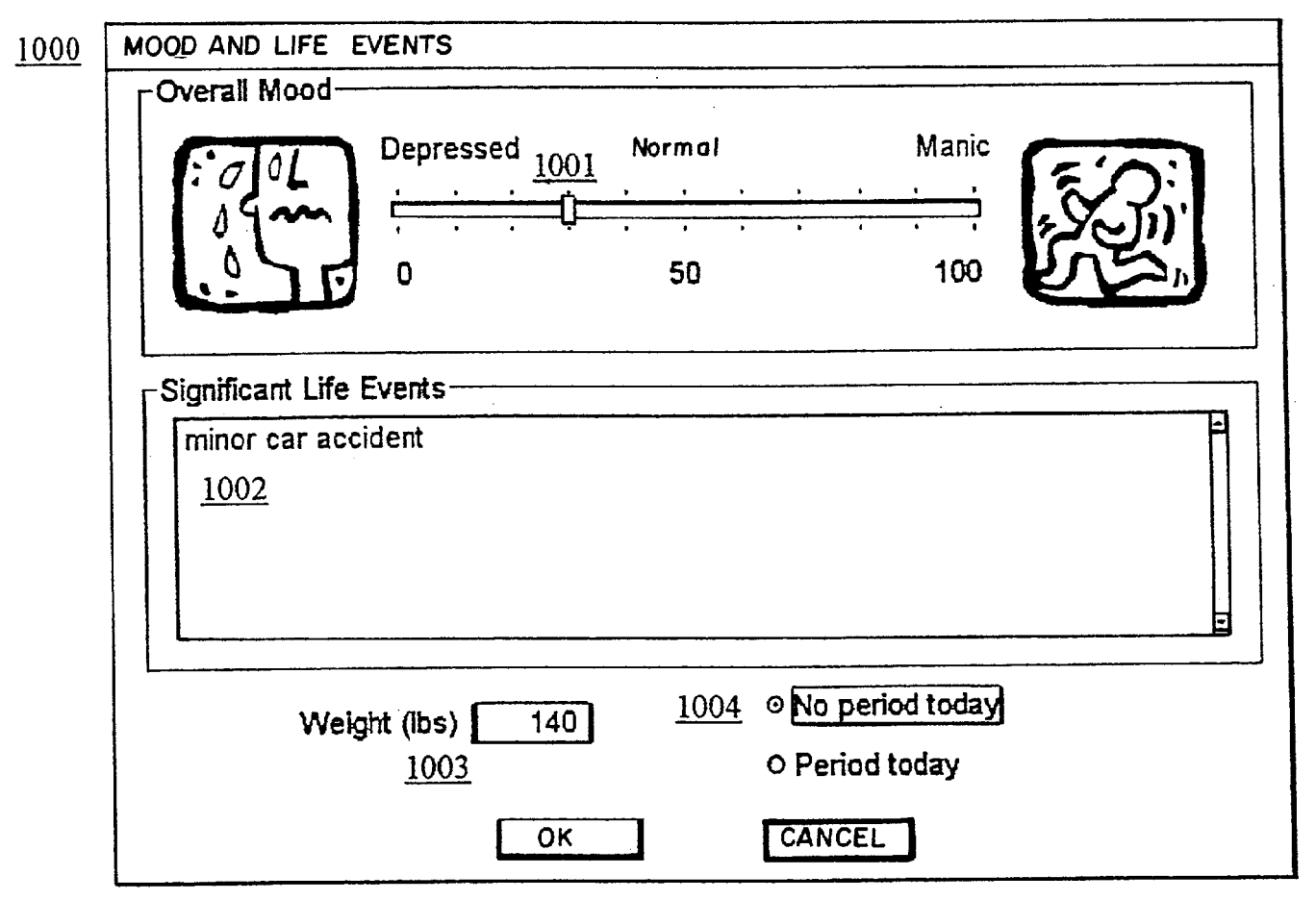

FIG. 10 shows an example of the mood dialog box for a female with VAS scale 1001 for entering mood, window 1002 shows the optional significant life events field, window 1003 is used for weight entry and buttons 1004 are used for answering the question regarding whether or not the patient is having a period today.

Figure 11:
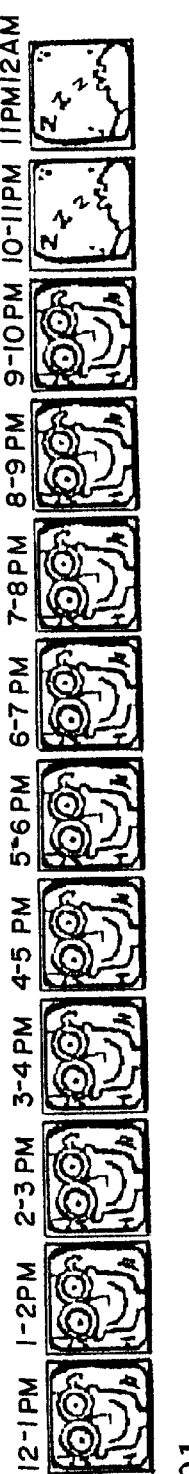
FIG. 11 illustrates the sleep dialog box of the patient data entry program of the present invention.
Figure 11:
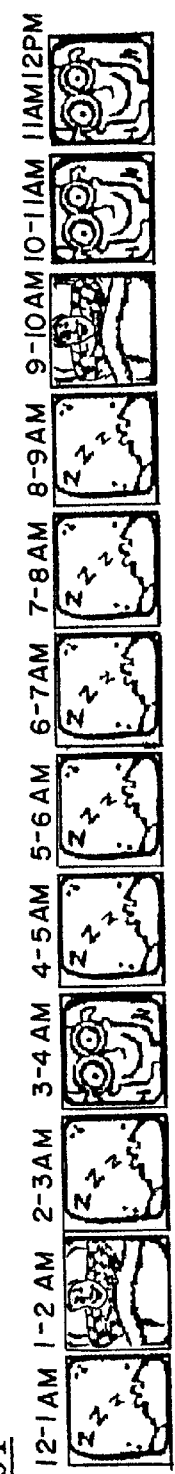
Figure 11:
Figure 11:
Figure 11:
Figure 11:
Figure 11:

FIG. 11 shows an example of the sleep dialog box with the 24 toggle switches 1101. The positions of the switch are as follows: awake icon 1102, in bed and asleep icon 1103 and in bed but awake icon 1104.

Figure 12:
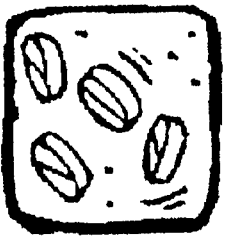
FIG. 12 illustrates the medications dialog box of the patient data entry program of the present invention.

FIG. 12 shows an example of the medication dialog box with medication name and strength 1201 and number of pills taken 1202.

Figure 13:
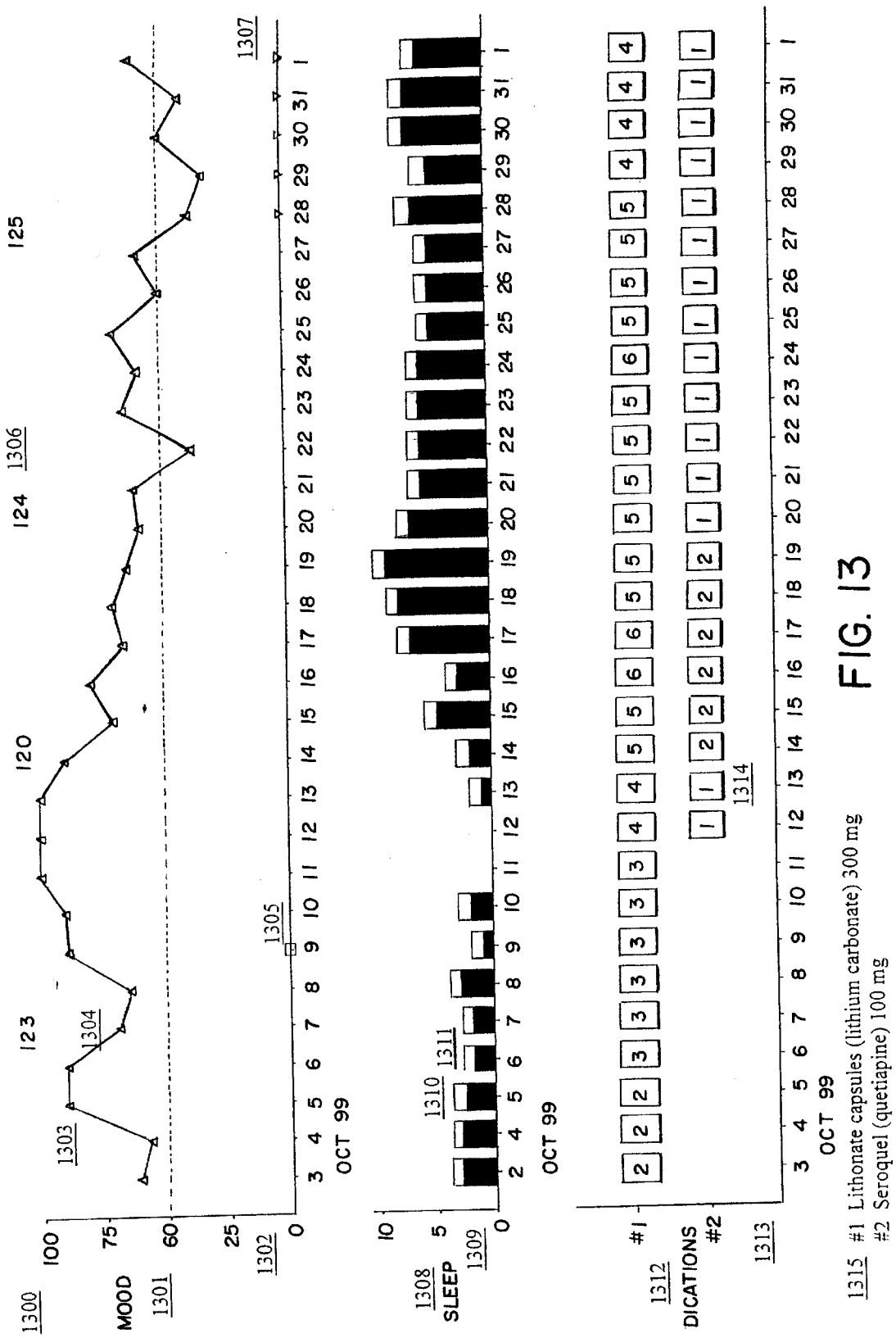
FIG. 13 is an exemplary 30-day printed mood chart created by the present invention.
Figure 14:
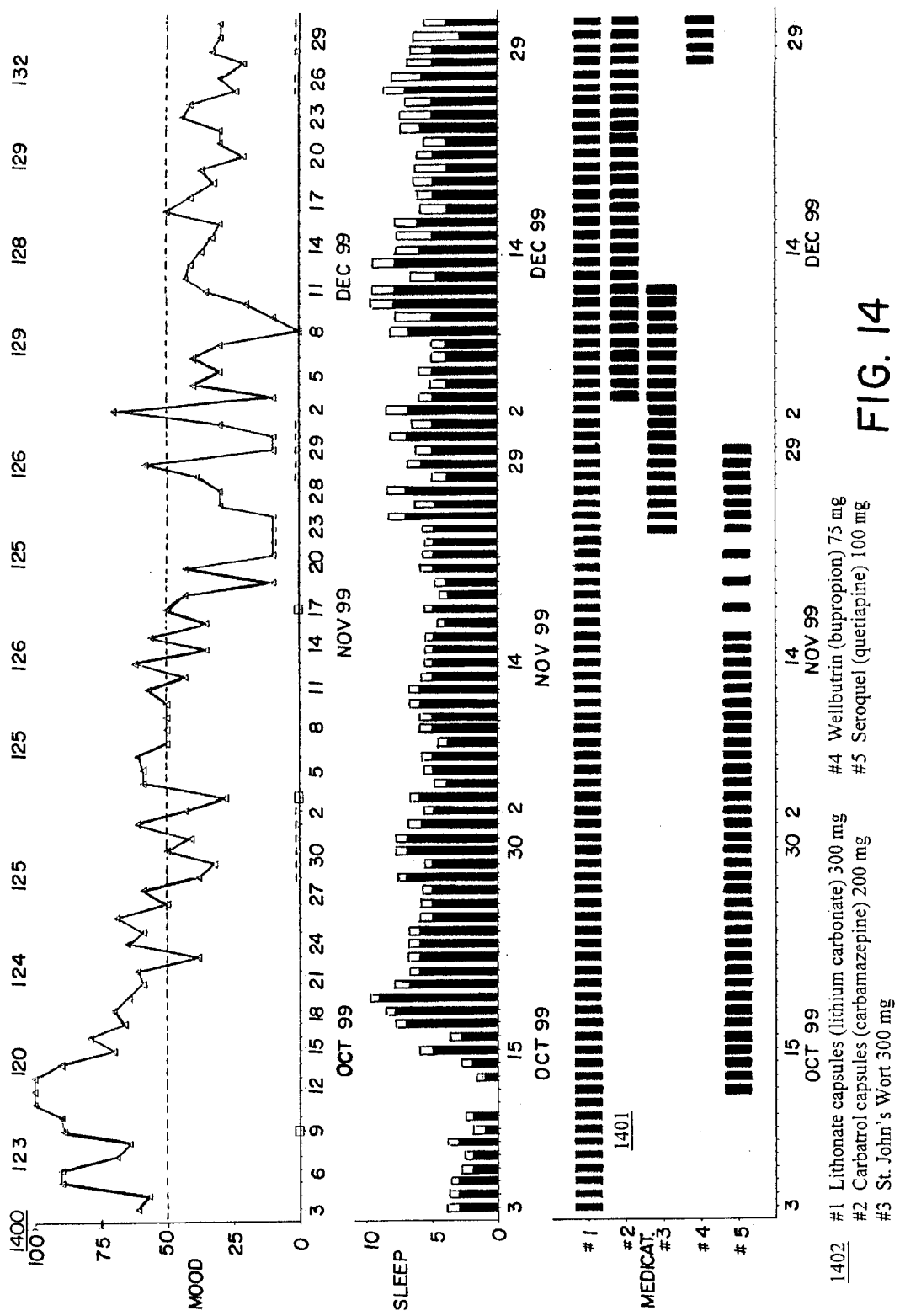
FIG. 14 is an exemplary 120-day printed mood chart created by the present invention.
Figure 15:
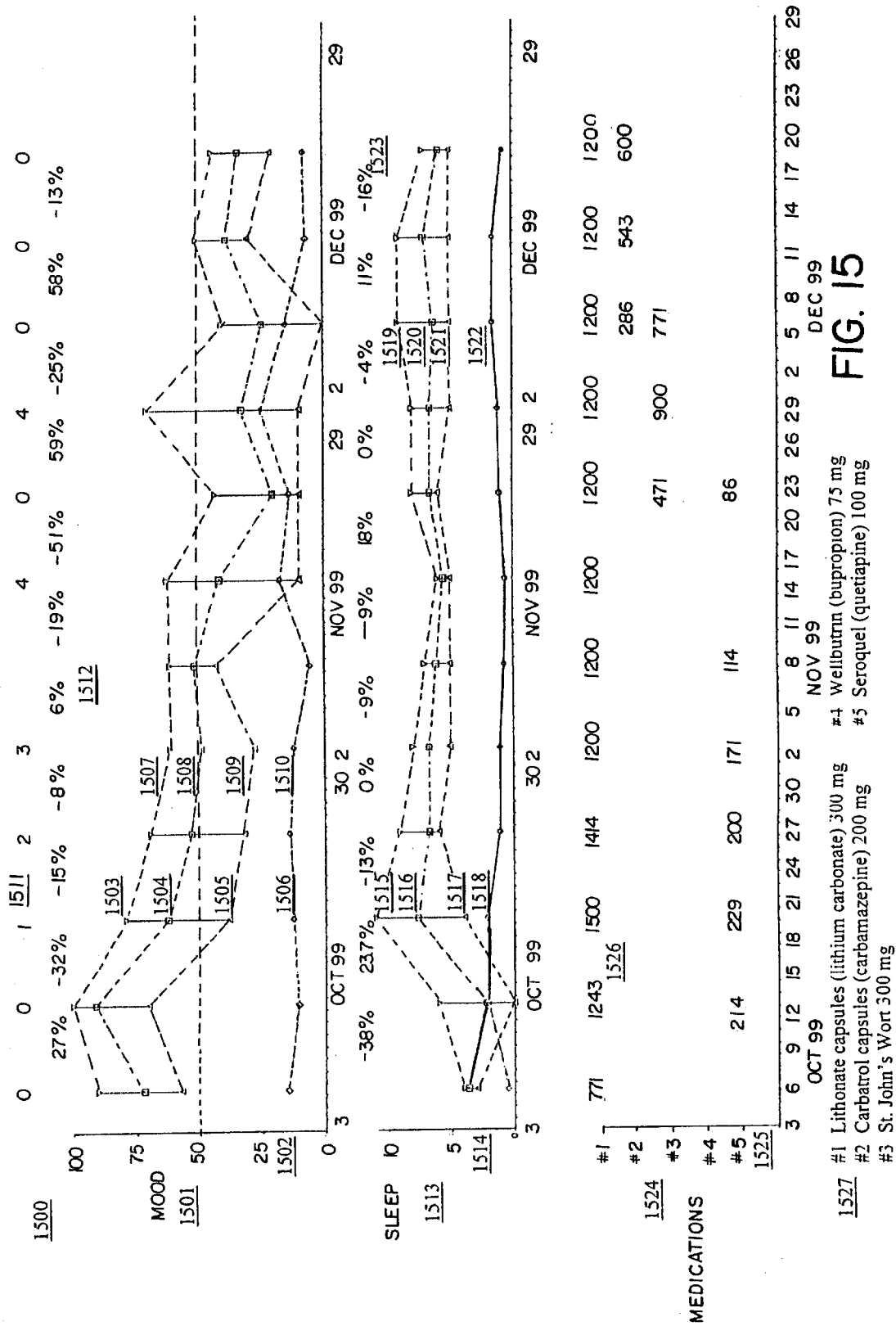
FIG. 15 is an exemplary 120-day, 7-day period statistical mood chart created by the present invention.

FIGS. 13 through 15 illustrate exemplary mood charts. On all of the charts, the data is displayed in three graphs: Mood versus Time, Sleep versus Time and Medications versus Time. All three graphs are directly aligned on the same horizontal axis equal to the time period selected for the chart (30, 60, 90, 120 or 180 days). For FIG. 13, 30 days is the selected time period. For FIGS. 14 and 15, 90 days is the selected time period.

Mood Versus Time Graph

In FIG. 13, mood chart 1300, the top graph Mood versus Time 1301 shows mood data over the 30-day time period selected. The vertical axis 1302 ranges between 0 and 100 with 50 representing normal mood, 0 the most depressed the patient has ever been and 100 the most manic the patient has ever been. Triangles 1303 show the mood value entered daily. The daily values are connected with a line 1304. Along the top of the graph, the patient's weight 1306 is entered once a week. If the patient entered a significant life event 1305, the date is outlined by a square on the horizontal axis. For female patients, days of menstrual period 1307 are outlined by an inverted triangle on the horizontal axis.

Sleep Versus Time Graph

The middle graph Sleep versus Time 1308 shows patient sleep data over the 30-day period selected. The vertical axis 1309 ranges between 0 and the total number of hours the patient was asleep plus in bed awake for the time period selected. The daily hours asleep 1310 are displayed as a dark colored bar topped by a lighter colored bar containing for any hours in bed awake 1311.

Medications Versus Time Graph

The bottom graph Medications versus Time 1312 shows which medications were taken each day by the patient for the time period selected. The vertical axis 1313 represents each of the different pills taken by the patient during the time period selected. Different pills may represent different medications or different strengths of the same medication.

A colored box appears for each medication 1314. The medications are displayed in the same color on all charts, arranged in medication class order alphabetically within each class. On the 30-day graph, the number of pills taken daily for each medication is shown in the middle of the color box 1314.

The specific medications are shown in the drug legend 1315. The numbers in the legend 1315 correspond to the numbers on the vertical axis of the graph 1313. Each number in the legend 1315 lists the specific medication and strength taken by the patient.

FIG. 14, mood chart 1400, is an example of a mood chart that extends for a 90-day period. The only difference from FIG. 13 is that the number of pills does not appear on the medication box 1401.

FIG. 15, mood chart 1500, is an example of a statistical chart calculated for a 7-day period and extending for 90 days. The statistical charts contain three graphs: Mood versus Time, Sleep versus Time and Medications versus Time. All three graphs are aligned on the same horizontal axis with the total number of days displayed. Calculations can be made for a 7 or 30-day period. The results are positioned in the middle of the period. For the 7-day period, the period extends from 3½ days before to 3/12 days after the displayed result.

Mood Versus Time Graph

The top graph Mood versus Time 1501 shows statistics based on mood data, calculated for a 7-day period. The vertical axis 1502 ranges between 0 and 100 with 50 representing normal mood. The 0 represents the most depressed while 100 represents the most manic the patient has ever been.

For each 7-day time period the following statistics are calculated:

| Statistics Calculated for Mood Data | Explanation |
| --- | --- |
| Maximum mood | Largest value entered for mood. |
| Mean mood | Average value entered for mood. |
| Minimum mood | Smallest value entered for mood. |
| Percent change in mean mood | Percent change in mean mood from the prior period. |
| Number of mood switches | The number of times the mood value crosses 50. |
| Standard deviation | A measure of the variability of the values entered. |

For each 7-day calculation, at least 5 days of mood data are required or the result is left blank. For each 30-day calculation, at least 20 days of mood data were entered or the result is left blank. For the count of mood switches, one or more blanks will restart the count.

In the middle of each 7-day period, the maximum mood will appear as an inverted triangle 1503, mean mood as a square 1504, and minimum mood as a triangle 1505. A dotted line connects the values in each period: 1507 connects the maximum mood from period to period, 1508 connects the mean mood from period to period and 1509 connects the minimum mood from period to period. Standard deviation 1506 is shown as a circle. A dotted line 1510 connects the standard deviation from period to period. On the top of the graph is the number of mood switches in the time period 1511, above the percent change in mean mood from period to period 1512.

Sleep Versus Time Graph

The middle graph 1513 shows statistics based on sleep data calculated for either a 7-day period and extending for either 60 or 90 days. The vertical axis 1514 ranges between 0 and the total number of hours the patient was asleep.

For each time period the following statistics are calculated:

| Statistics Calculated for Sleep Data | Explanation |
| --- | --- |
| Maximum sleep | Largest number of hours asleep. |
| Mean sleep | Average number of hours asleep. |
| Minimum sleep | Smallest number of hours asleep. |
| Percent change in mean sleep | Percent change in average number of hours asleep from the last period. |
| Standard deviation | A measure of the variability of the values entered. |

For each 7-day calculation, at least 5 days of sleep data are required or the result is left blank. For each 30-day calculation, at least 20 days of sleep data are required or the result is left blank.

In the middle of each 7-day period, the maximum sleep will appear as an inverted triangle 1515, mean sleep as a square 1516, and minimum sleep as a triangle 1517. A dotted line connects the values in each period: 1519 connects the maximum sleep from period to period, 1520 connects the mean sleep from period to period and 1521 connects the minimum sleep from period to period. Standard deviation 1518 is shown as a circle. A dotted line 1522 connects the standard deviation from period to period.

Medications Versus Time Graph

The bottom graph 1524 shows statistics based on medication data, calculated for either a 7-day period and extending for 120 days. The vertical axis 1525 represents each different medication taken. The drug legend 1527 numbers correspond to the numbers on the vertical axis of the graph 1525. Each number in the drug legend 1527 lists the specific medication and strength taken.

For each time period, the average dosage taken for each medication is calculated 1526. The calculations will include all strengths for the same medication. No averages are calculated for birth control pills, dermal patches or combination drugs.

For each 7-day calculation, at least 5 days of drug data were entered or the result is left blank. For each 30-day calculation, at least 20 days of drug data were entered or the result is left blank.

The methods and apparatus of the present invention, or certain aspects or portions thereof, may take the form of program code (i.e., instructions) embodied in tangible media, such as floppy diskettes, CD-ROMS, hard drives, or any other machine-readable storage medium, wherein, when the program code is loaded into and executed by a machine, such as a computer, the machine becomes an apparatus for practicing the invention. The methods and apparatus of the present invention may also be embodied in the form of program code that is transmitted over some transmission medium, such as over electrical wiring or cabling, through fiber optics, or via any other form of transmission, wherein, when the program code is received and loaded into and executed by a machine, such as a computer, the machine becomes an apparatus for practicing the invention. When implemented on a general-purpose processor, the program code combines with the processor to provide a unique apparatus that operates analogously to specific logic circuits.

Although the invention has been described with reference to a specific embodiment, this description is not meant to be construed in a limiting sense. Various modifications of the disclosed embodiment as well as alternative embodiments of the invention will become apparent to one skilled in the art upon reference to the description of the invention. It is therefore contemplated that the appended claims will cover any such modifications of embodiments that fall within the true scope of the invention.

BIBLIOGRAPHY

References cited in the Specification are as follows:

Aagaard J, Vestergaard P, Maargjerg K. Adherence to lithium prophylaxis: 1. Clinical predictors and patient's reasons for nonadherence. Pharmacopsychiatry 1988;21:121–125.

American Psychiatric Association. Diagnostic and statistical manual of mental disorders, 4th revision (DSM-IV). Washington: American Psychiatric Press, 1994a.

Bauer M S, Crits-Christoph P, Ball W A, Dewees E, McAllister T, Alahi P, Cacciola J, Whybrow P C. Independent assessment of manic and depressive symptoms by self-rating. Scale characteristics and implications for the study of mania. Arch Gen Psychiatry 1991;48:807–812.

Berghofer A, Kossmann B, Muller-Oerlinghausen B. Course of illness and pattern of recurrences in patients with affective disorders during long-term lithium prophylaxis: a retrospective analysis over 15 years. Acta Psychiatr Scand 1996;93:349–54.

Broadhead W E, Blazer D G, George L K, Tse C K. Depression, disability days, and days lost from work in a prospective epidemiologic survey. JAMA 1990;21:2524–8.

Coryell W, Scheftner W, Keller M, Endicott J, Maser J, Kiernan G L. The enduring psychosocial consequences of mania and depression, Am J Psychiatry 1993; 150:720–7.

Denicoff K D, Smith-Jackson E E, Disney E R, Suddath R L, Leverich G S, Post R M. Preliminary evidence of the reliability and validity of the prospective life-chart methodology (LCM-p). J Psychiatr Res 1997;31:593–603.

Fava G A. Subclinical symptoms in mood disorders: Pathophysiological and therapeutic implications. Psychol Med 1999;29:47–61.

Gitlin M J, Swendsen J. Heller T L, Hammen C. Relapse and impairment in bipolar disorder. Am J Psychiatry 1995;152:1635–40.

Goodwin F K, Jamison K R. Manic-Depressive Illness. New York: Oxford University Press, 1990.

Greenberg P E, Stiglin L E, Finkelstein S N, Berndt E R. Depression: a neglected major illness. J Clin Psychiatry 1993;54:419–24.

Keller M B, Lavori P W, Coryell W, Endicott J, Mueller Ti. Bipolar 1: a five-year prospective follow-up. J Nerv Ment Dis 1993; 1 81:238–45.

Keller M B, Lavori P W, Mueller Ti, Endicott J, Coryell W, Hirshfield R M, Shea T. Time to Recovery, chronicity, and levels of psychpathology in major depression. A 5-year prospective follow-up of 431 subjects. Arch Gen Psychiatry 1992;49:809–16.

Keller M B, Shapiro R W. "Double depression": superimposition of acute depressive episodes on chronic depressive disorders. Am J Psychiatry 1982; 1 39:438–42.

Kessler R C, McGonagle K A, Zhao S, Nelson C B, Hughes M, Eshleman S, Wiftchen H U, Kendler K S. Lifetime and 12-month prevalence of I) SM-111-R psychiatric disorders in the United States. Results from the National Comorbidity Survey. Arch Gen Psychiatry 1994;51:8–19

Leibenluft E, Ashman S B, Feldman-Naim S, Yonkers K A. Lack of relationship between menstrual cycle phase and mood in a sample of women with rapid cycling bipolar disorder. Biol Psychiatry 1999;46:577–580.

Leverich G S, Post R M. Life charting the course of bipolar disorder. Curr Rev Mood Anxiety Disord 1996;1:48–61.

Mueller Ti, Leon A C, Keller M B, Solomon D A, Endicott J, Coryell W, Warshaw M, Maser J D. Recurrence after recovery from major depressive disorder during 15 years of observational follow-up. Am J Psychiatry 1999; 156 (7):1000–6.

Murray C J, Lopez A D. Evidence-based health policy— lessons from the GLobal Burden of Disease Study. Science 1996;274:1593–4.

Post R M, Leverich G S, Denicoff K D, Frye M A, Kimbrell T A, Dunn R. Alternative approaches to refractory depression in bipolar illness. Depression Anxiety 1997;5:175–189.

Schumann C, Lenz G, Berghofer A, Muller-Oerlinghausen B. Non-adherence with long-term prophylaxis: a 6-year naturalistic follow-up study of effectively ill patients. Psychiatry Res 1999;89:247–57.

Simon S E, VonKorff M, Wagner E H, Barlow W. Patterns of antidepressant use in community practice. Gen Hops Psychiatry 1993;15:399–408.

Thase, M. E., & Sullivan, L. R. (I 995). Relapse and recurrence of depression: A practical approach for prevention. CNS Drugs, 4, 261–277.

Tohen M, Waternaux C S, Tsuang M T. Outcome in Mania; a 4-year prospective followup of 75 patients utilizing survival analysis. Arch Gen Psychiatry 1990;47:1106–1 1 1 1.

Wells K B, Stewart A, Hays R D, Burnam M A, Rogers W, Daniels M, Berry S, Greeenfield S, Ware J. The functioning and well-being of depressed patients. Results from the medical Outcomes Study. JAMA 1990;262:914–919.

Wyatt R J, Henter 1. An economic evaluation of manic-depressive illness—1991. Soc Psychiatry Psychiatr Epidemiol 1995;20:213–219.

What is claimed is:

1. In a computer system having a storage device, a method for gathering clinical data useful in the clinical analysis and treatment of mood disorders, said method comprising the steps of:
   a. displaying a main menu including a multiplicity of icons depicting inquiries to be answered by a patient;
   b. storing said patient's answers to said inquiries as clinical data generated on a regular basis by said patient; and
   c. creating longitudinal charts and statistics based on selections made by the patient over a single 24-hour period.

2. The method as in claim 1 further comprising the step of selecting a point on a scale depicting said patient's current mood.

3. The method as in claim 1 further including the step of selecting a sleep icon for each hour of a 24 hour period for updating sleep data.

4. The method as in claim 1 further including the step of selecting a medication icon for updating type and amount of medication taken.

5. The method as in claim 1 further including the step of creating longitudinal charts and statistics based on selections made by said patient over a given period of time.

6. The method as in claim 1 wherein said patient makes selections for sleep for every hour of every day.

7. The method as in claim 1 further including the step of aggregating data received from a plurality of patients.

8. The method as in claim 7 further including for female patients selecting an indicator for updating menstrual cycle data.

9. The method as in claim 7 further including selecting an indicator for updating said patient's weight on a weekly basis.

10. A program storage medium encoded with machine-readable computer program code for gathering clinical data useful in the clinical analysis and treatment of mood disorders, when the program code is executed by a computer, the computer performs the steps:
    a. displaying a main menu including a multiplicity of icons depicting inquiries to be answered by a patient;
    b. storing said patient's answers to said inquiries as clinical data generated on a regular basis by said patient; and
    c. aggregating data received from a plurality of patients.

11. The medium as in claim 10 further including the step of selecting a point on a scale depicting said patient's current mood.

12. The medium as in claim 10 further including the step of selecting a sleep icon for updating sleep data.

13. The medium as in claim 10 further including the step of selecting a medication icon for updating type and amount of medication taken.

14. The medium as in claim 10 further including the step of creating longitudinal charts and statistics based on selections made by said patient over a given period of time.

15. The medium as in claim 14 wherein said given period of time is a single 24-hour period.

16. The medium as in claim 10 wherein said patient makes selections for sleep for every hour of every day.

17. The medium as in claim 10 further including for female patients selecting an indicator for updating menstrual cycle data.

18. The medium as in claim 10 further including selecting an indicator for updating said patient's weight on a weekly basis.

19. A method for recording clinical data using a computer system, which data is useful in the analysis and treatment of mood disorders, said method comprising the steps of:
    a. displaying a main menu including a multiplicity of icons for selection by a patient;
    b. selecting a point on a mood scale ranging from depressed to manic in order to update mood data;
    c. selecting a sleep icon based on the number of hours asleep and the number of hours in bed and not asleep for updating sleep data;
    d. selecting a medication icon and updating the medication dosage taken; and,
    e. relaying said recorded clinical data to an attending physician.

20. The method as in claim 19 further including the step of selecting an icon indicative of one of the following: being awake, asleep or in bed and awake, and updating during a given period of time.

21. A program storage medium encoded with machine-readable computer program code for recording clinical data using a computer, which data is useful in the analysis and treatment of mood disorders, when the program code is executed by said computer, the computer performs the steps of:
    a. displaying a main menu including a multiplicity of icons for selection by a patient;
    b. selecting a point on a mood scale ranging from depressed to manic in order to update mood data;
    c. selecting a sleep icon based on the number of hours asleep and the number of hours in bed and not asleep for updating sleep data;
    d. selecting a medication icon and updating the medication dosage taken; and,
    e. relaying said recorded clinical data to an attending physician.

22. The medium as in claim 21 further including the step of selecting an icon indicative of one of the following: being awake, asleep or in bed and awake, and updating during a given period of time.

23. A method for creating a combined longitudinal chart of clinical data received from a patient using a computer system, which data is useful in the clinical analysis and treatment of mood disorders, said method comprising the steps of:
    a. plotting a first graph of said patient's mood for each day based upon a selection by said patient of a point on a mood scale ranging from depressed to manic;
    b. plotting a second graph of said patient's sleep pattern for each day based upon a selection by said patient of a sleep icon; and
    c. plotting a third graph of medication taken by said patient by selecting an icon indicative of the medication dosage taken each day.

24. A method for aggregating longitudinal clinical data received from patients using a computer system, which data is useful in the clinical analysis and treatment of mood disorders, said method comprising the steps of:

a. for each patient submitting clinical data, plotting a first graph of said paitient's mood for each day based upon a selection by said patient of a point on a mood scale ranging from depressed to manic, thereby forming an overlay of first graphs for each patient;

b. for each patient submitting clinical data, plotting a second graph of said patient's sleep pattern for each day based upon a selection by said patient of a sleep icon, thereby forming an overlay of second graphs for each patient; and c. for each patient submitting clinical data, plotting a third graph of medication taken by said patient by selecting an icon indicative of the medication dosage taken each day, thereby forming an overlay of third graphs for each patient.

* * * * *